United States Patent
Hyman

(10) Patent No.: US 6,488,698 B1
(45) Date of Patent: Dec. 3, 2002

(54) PORTABLE LIGHT UNIT FOR TREATMENT OF SEASONAL AFFECTIVE DISORDERS

(75) Inventor: Henry H. Hyman, P.O. Box 216, Owings Mills, MD (US) 21117

(73) Assignee: Henry H. Hyman, Pikesville, MD (US)

(*) Notice: Subject to any disclaimer, the term of this patent is extended or adjusted under 35 U.S.C. 154(b) by 45 days.

(21) Appl. No.: 09/639,643

(22) Filed: Aug. 16, 2000

(51) Int. Cl.[7] ............................................. A61N 5/006
(52) U.S. Cl. ............................. 607/91; 607/88; 607/90; 600/26
(58) Field of Search ................... 607/88, 90, 91, 607/93–95, 108–110; 326/103–106; 600/26, 22

(56) References Cited

U.S. PATENT DOCUMENTS

| | | | | |
|---|---|---|---|---|
| 4,911,166 A | * | 3/1990 | Leighton et al. | 128/380 |
| 5,149,184 A | * | 9/1992 | Hughes et al. | 362/1 |
| 5,197,941 A | * | 3/1993 | Whitaker | 600/27 |
| 5,447,527 A | | 9/1995 | Waldman | |
| 5,562,719 A | * | 10/1996 | Lopez-Claros | 607/88 |
| 5,824,024 A | * | 10/1998 | Dial | 607/88 |
| 5,919,217 A | | 7/1999 | Hughes | |
| 6,235,046 B1 | * | 5/2001 | Gerdt | 607/88 |

FOREIGN PATENT DOCUMENTS

| | | |
|---|---|---|
| DE | 4433291 | 3/1996 |
| DE | 19836312 | 2/2000 |
| WO | WO 89/08475 | 9/1989 |
| WO | WO 96/14899 | 5/1996 |

* cited by examiner

*Primary Examiner*—Linda C. M. Dvorak
*Assistant Examiner*—A. Farah

(57) ABSTRACT

A portable light unit for treatment of seasonal affective disorders. The portable device is carried in a small case having four bulbs capable of emitting full spectrum light at 10,000 lux intensity for each therapy session. Therefore, the device can be carried by the patient or the physician to the patient.

5 Claims, 2 Drawing Sheets

PORTABLE LIGHT UNIT FOR TREATMENT OF SEASONAL AFFECTIVE DISORDERS

BACKGROUND OF THE INVENTION

1. Field of the Invention

The present invention relates generally to an illumination device. More specifically, the invention is a portable briefcased illumination device for treatmemt of seasonal affective disorders.

2. Description of the Related Art

The relative art of interest describes various illumination devices, but none discloses the present invention. There is a need for a portable illumination device adapted to treat seasonal affective syndromes and disorders.

The related art will be discussed in the order of perceived relevance to the present invention.

U.S. Pat. No. 5,149,184 issued on Sep. 22, 1992, to Philip Hughes et al. describes a combined work station and phototherapy unit in which the light source is cantilevered at adjustable angles on a rotatable flat lid containing a plurality of fluorescent tubes and ballasts behind a diffuser panel. A switching arrangement can turn on two lamps (3,300 lux), four lamps (6,600 lux) or six lamps (10,000 lux) via a power cord. The work stations can vary in size from 2 ft. square, 1 ft. by 3 ft. and 10 inches by 3 ft. The work station is distinguishable for its limitation to a large boxed unit with a cantilevered illuminating panel.

U.S. Pat. No. 5,919,217 issued on Jul. 6, 1999, to Philip C. Hughes describes a portable therapy light housed in a rectangular box of molded plastic having a cutout for the eyes and an bridge for resting the device on the patient's nose. Two side arms for, the ears are also provided. The illumination source is either a twin-tubed fluorescent lamp or a single incandescent lamp powered 10 by either A.C. voltage or batteries. The device is distinguishable for its boxed eyeglass type structure with conventional illumination sources.

U.S. Pat. No. 5,447,527 issued on Sep. 5, 1995, to Murray M. Waldman describes a therapeutic light device comprising a light bulb in a light fixture emitting only a wavelength of 490–520 nanometers and restricting the light energy radiance to between 1.8 to 200 microwatts per square centimeter over the eyes of the patient. The light restricting apparatus can be a narrowband light transmission filter placed strategically over the upper portion or the phosphor of a fluorescent bulb. The device is distinguishable for its restrictive light tolerance, two-part illumination and the use of a fluorescent light source.

U.S. Pat. No. 5,197,941 issued on Mar. 30, 1993, to Barbara Whitaker describes a portable device for controlling circadian rhythm disorders comprises the following components in a plastic molded box having a curved lid with an undefined reflective concave surface and an external ion generator connected by an extension cord. The box contains a fluorescent lamp energized by either 120 volts A.C. or an integrated battery. A progammable microprocessor controls a liquid crystal clock display module and a speaker. On/off control switches include a sleep function switch, an override switch for lamp control, a switch for the ion generator, and a volume control for the speaker. The device is distinguishable for its manifold features limited to a single fluorescent lamp.

U.S. Pat. No. 4,911,166 issued on Mar. 27, 1990, to Stephen B. Leighton et al. describes a portable light delivery system using a point source of light from a high intensity halogen or incandescent bulb and directing a large fraction of the light directly into the patient's eyes without focusing the light to my cause visual damage. A helmet has two anchored assemblies suspended in front of the patient. Each light assembly has a light source bouncing its illumination from a concave mirror rear wall to a positive convex lens. The device is distinguishable for its reliance on a pair of suspended light sources with a frontal lens.

U.S. Pat. No. 5,562,719 issued on Oct. 8, 1996, to Marcelo E. Lopez-Claros describes a light therapy apparatus comprising a mask which provides illumination by adjustably dividing the visual field of each eye into temporal and nasal visual fields by internal walls. The two individual sources of illumination are fluorescent light bulbs having an intensity of 2,500 to 10,000 lux. The apparatus is distinguishable for its required segmented aspect for illumination of each eye.

U.S. Pat. No. 5,824,024 issued on Oct. 20, 1998, to Daniel C. Dial describes illumination devices for treating light deficiency and mood disorders including color therapy. The illumination fixture contains a convoluted arrangement of neon gas and mercury containing tubing and optionally with optic cables. The rectangular light reflecting back surface is white plexiglass. The device is distinguishable for its requirement for fluorescent lighting arranged in a convoluted pattern.

W.I.P.O. Patent Application No. WO 89/08475 published on Sep. 21, 1989, for George C. Brainard describes a portable phototherapeutic device incorporated in a cap to emit at least 200 lux light on the eyes of the wearer. The preferred embodiment employs a conical canopy to focus the light from a quartz halogen lamp positioned in front and controlled by a rheostat control located on the side of the cap for obtaining a preferred 2,000 to 2,500 lux intensity. A battery pack is housed under the cap in the rear. A second embodiment employs the batteries under the top of the hat and suspends the lamp underneath an extension. A third embodiment poaitions the lamp above a rectangular radiation shield. A fourth embodiment employs a lamp above the visor of a sun visor cap and a remote control wired to the lamp. The devices are distinguishable for their restriction to caps having a quartz halogen lamp.

W.I.P.O. Patent Application No. WO 96/14899 published on May 23, 1996, for Optomed Opto Medical Systems GMBH describes a light therapy device comprising fluorescent lamps of different mono-chromatic radiation used in combination with a prior application of a light-sensitizing ointment. The device is distinguishable for its requirement for fluorescent lamps of different monochromatic radiation.

German Patent Application No. DE 44 33 291 A1 published on Mar. 21, 1996, for Hans-Jurgen Hentschel describes as best understood a rectangular light box containing at least four daylight lamps in individual apertured concave reflector elements with the apertures aligned with slits in the rear of the box. The front of the box is closed with a glass pane. The light box is distinguishable for its individual lamp reflecting surfaces.

German Patent Application No. 198 36 312 A1 published on Feb. 24, 2000, for Hans-Peter Reuter describes a lamp having a spectrum corresponding to natural daylight comprising three fluorescent light tubes behind a housing which includes a plurality of elongated hollow (triangular in cross-section) reflector elements having colored surfaces which match the spectrum of the light sources. A microprocessor is included. The lamp is distinguishable for its unique lamp and reflector structure and microprocessor control.

None of the above inventions and patents, taken either singularly or in combination, is seen to describe the instant invention as claimed. Thus, a portable light unit for treatment of seasonal affective disorders solving the aforementioned problems is desired.

SUMMARY OF THE INVENTION

The present invention is directed to a portable illumination device for the treatment of seasonal affective disorders. The portable device is carried in a small hard covered case having four bulbs capable of emitting full spectrum light at 10,000 lux intensity for each therapy session. Therefore, the device can be carried by the patient or the physician to the patient.

Accordingly, it is a principal object of the invention to provide a portable illumination device.

It is another object of the invention to provide a portable illumination device capable of treating seasonal affective disorders.

It is a further object of the invention to provide a portable illumination device capable of treating seasonal affective disorders having four bulbs capable of emitting full spectrum light at 10,000 lux intensity for each therapy session.

Still another object of the invention is to provide a portable illumination device capable of treating seasonal affective disorders carried in a hard covered briefcase having a rear mirror.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features is consistently throughout the attached drawings.

DETAILED DESCRIPTION OF THE PREFERRED EMBODIMENT

Figure 1:
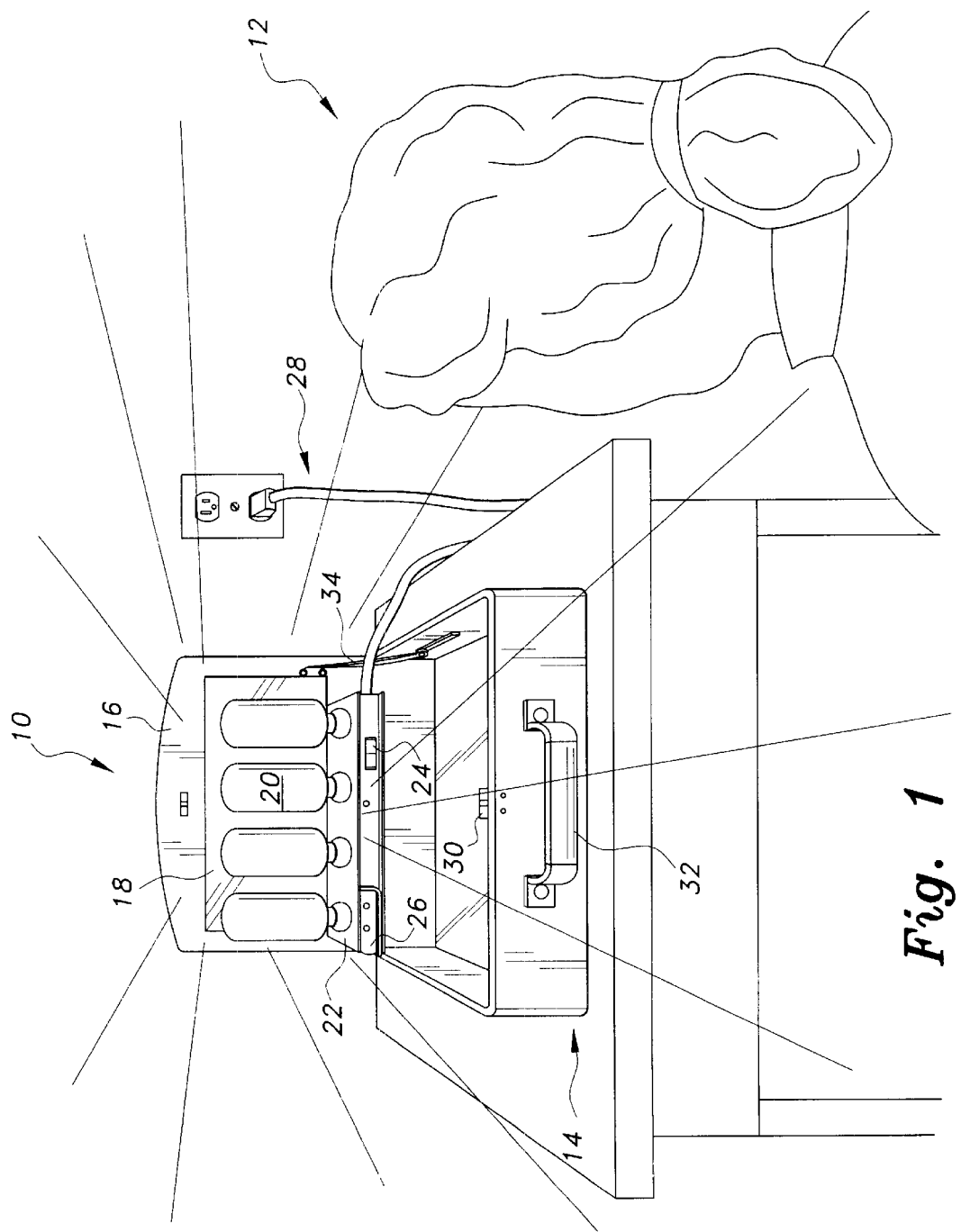
FIG. 1 is an environmental, perspective view of a portable light unit ready for treatment of seasonal affective disorders according to the present invention.
Figure 2:
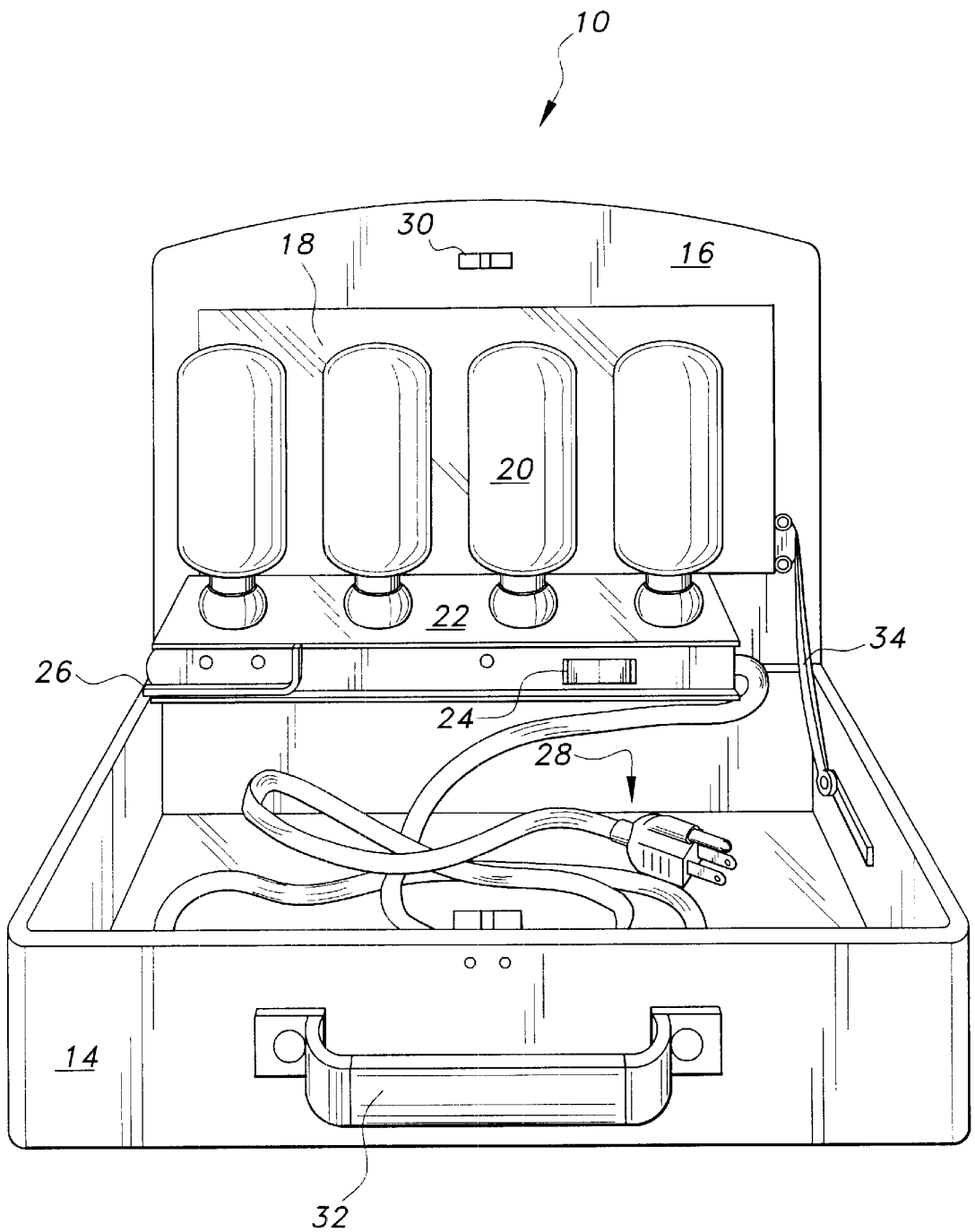
FIG. 2 is an enlarged perspective view of the open hard covered briefcase including the mirror, lamps and electric cord.

In FIGS. 1 and 2, a portable light unit 10 for treatment of seasonal affective disorders of a patient 12 comprises a rectangular hard plastic covered briefcase 14 having the inside surface of a rear cover 16 covered with a plastic mirror 18. A plurality of screw-in illumination lamps 20, i.e., four, including a ballast element (hidden) in each lamp is arranged in a line parallel to the mirror 18 and on a polished metal base 22 which has an on/off lamp switch 24 and a slide lock 26 to hold the cover 16 open at a perpendicular angle. A grounded electric extension cord with plug 28 is included for supplying house current to the lamps 20. Other briefcase 14 appurtenances include a latch 30, a handgrip 32 and a cover hinge 34.

The lamps 20 and mirror 18 illuminate at least 10,000 lux and have visible spectrum capacity. The oblong lamps 20 inherently supply the lens for the required illumination, thereby eliminating the need for extra focusing capacity, i.e., the unit 10 is devoid of any external focusing lens.

The total weight of the unit 10 is less than five pounds and has the following exemplary dimensions: 15 inches long, 7 inches wide and 3.5 inches deep.

The unit 10 can consequently be hand carried and used by the patient 12 or carried to the patient by the attending physician. The unit 10 is simplified and economical because it does not contain intricate controls required by the prior art.

It is to be understood that the present invention is not limited to the embodiment described above, but encompasses any and all embodiments within the scope of the following claims.

I claim:

1. A portable light unit for treatment of seasonal affective disorders, said portable light unit consisting of:

a rectangular hard covered briefcase including a hingedly attached cover having an interior surface;

a planar mirror attached to the interior surface of said cover;

a polished metal base extending from the interior surface of said cover beneath said mirror, said base including an on/off switch and an electrical cord; and four illumination lamps extending upward from said base, said lamps being arranged in a line parallel to said mirror such that said lamps and said mirror provide an illumination of at least 10,000 lux.

2. The portable light unit according to claim 1, wherein said lamps include screw-in lamps, each having an oblong configuration.

3. The portable light unit according to claim 1, wherein said base further includes a slide lock to retain said cover in an opened position.

4. The portable light unit according to claim 1, wherein said unit has a total weight of less than five pounds.

5. The portable light unit according to claim 1, wherein said unit has a length of 15 inches, a width of 7 inches and a depth of 3.5 inches.

* * * * *